US010653877B2

(12) United States Patent
Kratzberg et al.

(10) Patent No.: US 10,653,877 B2
(45) Date of Patent: May 19, 2020

(54) PROSTHESIS DELIVERY DEVICE WITH DETACHABLE CONNECTOR ASSEMBLY

(71) Applicant: Cook Medical Technologies LLC, Bloomington, IN (US)

(72) Inventors: Jarin A. Kratzberg, West Lafayette, IN (US); Ryan C. Bradway, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 139 days.

(21) Appl. No.: 15/872,404

(22) Filed: Jan. 16, 2018

(65) Prior Publication Data

US 2018/0200496 A1    Jul. 19, 2018

Related U.S. Application Data

(60) Provisional application No. 62/448,106, filed on Jan. 19, 2017.

(51) Int. Cl.
*A61M 39/10* (2006.01)
*A61M 25/06* (2006.01)
(Continued)

(52) U.S. Cl.
CPC ............. *A61M 39/10* (2013.01); *A61F 2/966* (2013.01); *A61M 25/0097* (2013.01);
(Continued)

(58) Field of Classification Search
CPC ............ A61F 2/966; A61F 2002/9517; A61M 25/0097; A61M 25/0113; A61M 25/0136; A61M 25/0662; A61M 25/09041; A61M 29/02; A61M 39/10; A61M 39/1011; A61M 39/02; A61M 2039/1027
See application file for complete search history.

(56) References Cited

U.S. PATENT DOCUMENTS 5,201,757 A *  4/1993  Heyn ........................ A61F 2/95
                                                              606/198
5,713,854 A *  2/1998  Inderbitzen ......... A61M 25/104
                                                              604/509

(Continued)

OTHER PUBLICATIONS

European Search Report for corresponding EP Application No. 18275007 dated May 17, 2018, 7 pages.

*Primary Examiner* — Jocelin C Tanner
(74) *Attorney, Agent, or Firm* — Brinks Gilson & Lione

(57) ABSTRACT

A prosthesis delivery device and method are described herein. An elongate sheath extends about a longitudinal axis, and a hub is coupled to the sheath. A handle is distal to the hub, and a connector assembly is coupled to a proximal end of the handle. The connector assembly is removably coupled to the hub, and the connector assembly includes a longitudinal passageway defined therein in communication with the longitudinal hub lumen. In one aspect, the connector assembly includes a plurality of jaw elements, and an actuating ring operable to move the jaw elements between the attachment configuration where the jaw elements are coupled to the hub, and the detachment configuration where the jaw elements are radially displaced and decoupled from the hub to remove a component from the sheath lumen.

14 Claims, 8 Drawing Sheets

(51) Int. Cl.
    *A61M 25/00* (2006.01)
    *A61F 2/966* (2013.01)
    *A61M 25/09* (2006.01)
    *A61M 25/01* (2006.01)
    *A61M 29/02* (2006.01)
    *A61F 2/95* (2013.01)

(52) U.S. Cl.
    CPC .... *A61M 25/0113* (2013.01); *A61M 25/0136* (2013.01); *A61M 25/0662* (2013.01); *A61M 25/09041* (2013.01); *A61M 39/1011* (2013.01); *A61F 2002/9517* (2013.01); *A61M 29/02* (2013.01); *A61M 2039/1027* (2013.01)

(56) References Cited

U.S. PATENT DOCUMENTS

| | | | |
|---|---|---|---|
| 6,217,586 B1 | 4/2001 | Mackenzie | |
| 6,273,895 B1 | 8/2001 | Pinchuk et al. | |
| 7,819,882 B2 | 10/2010 | Rourke | |
| 2012/0226341 A1* | 9/2012 | Schreck | A61F 2/966 623/1.12 |
| 2012/0290066 A1* | 11/2012 | Nabulsi | A61F 2/966 623/1.11 |
| 2013/0261726 A1 | 10/2013 | Alger et al. | |

\* cited by examiner

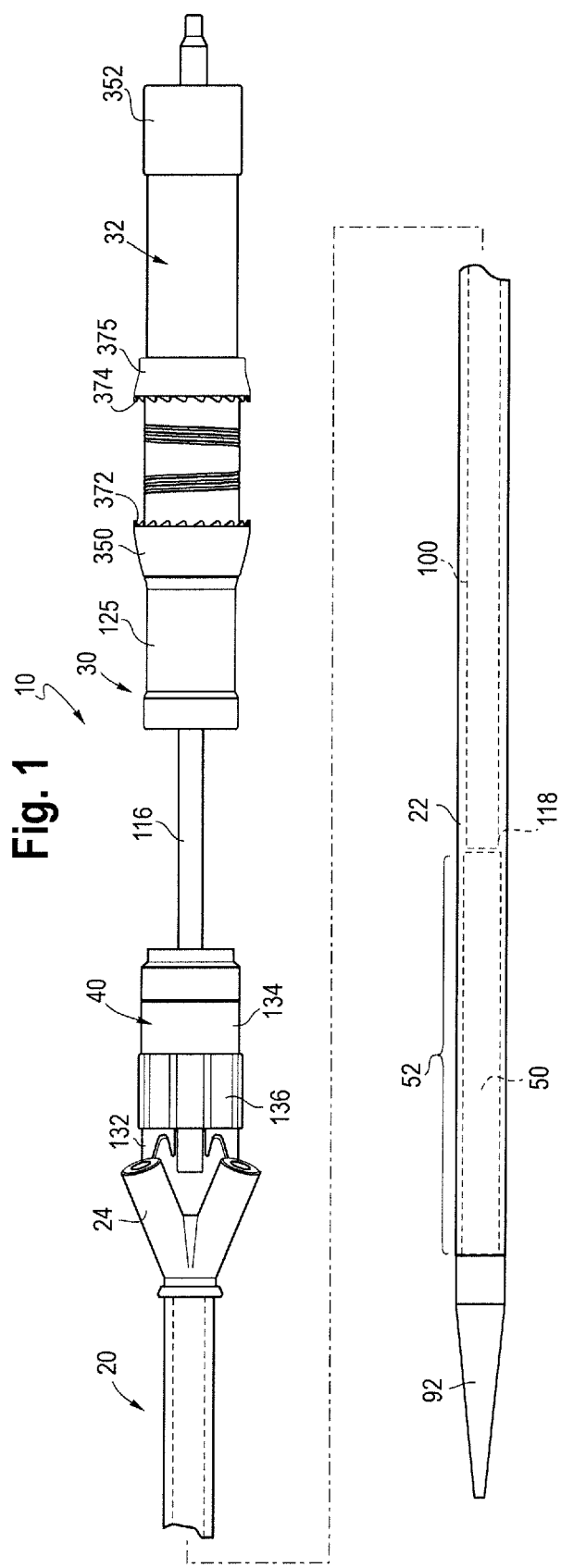

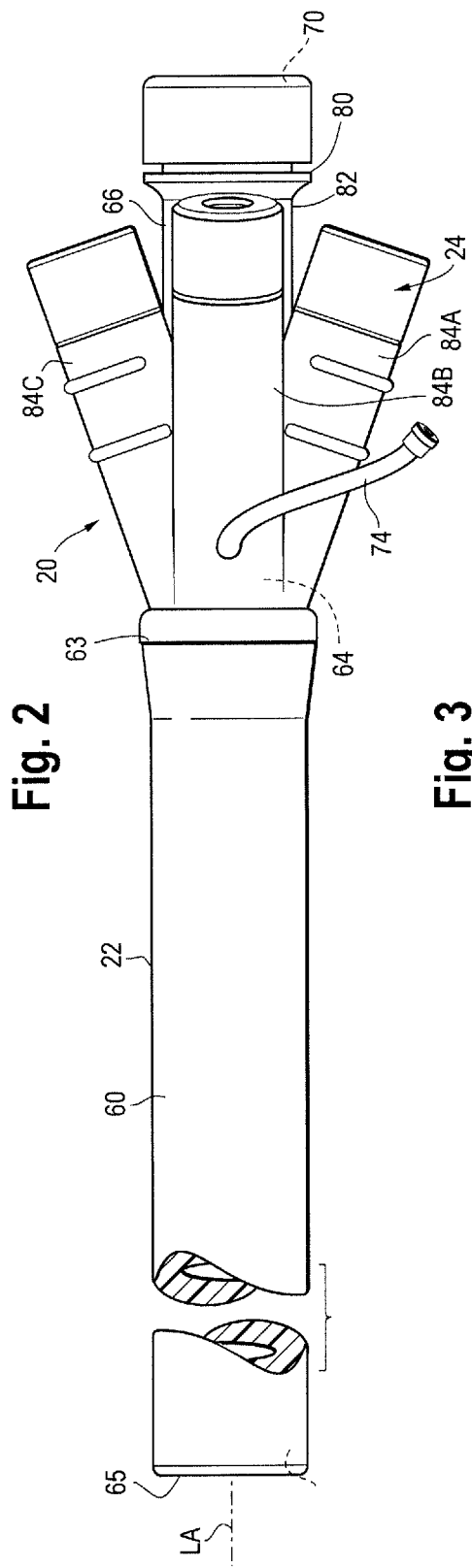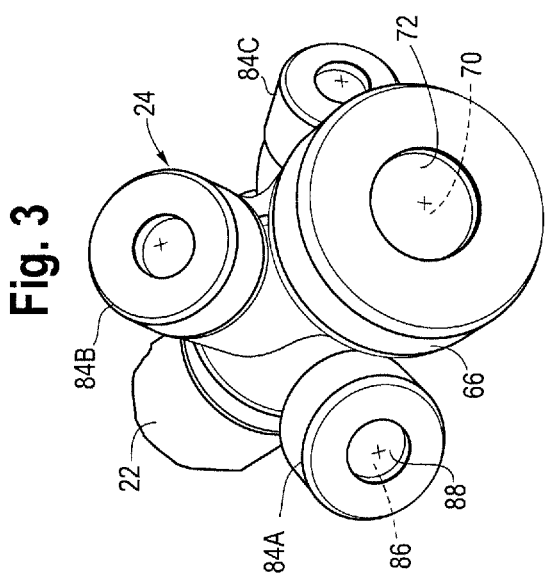

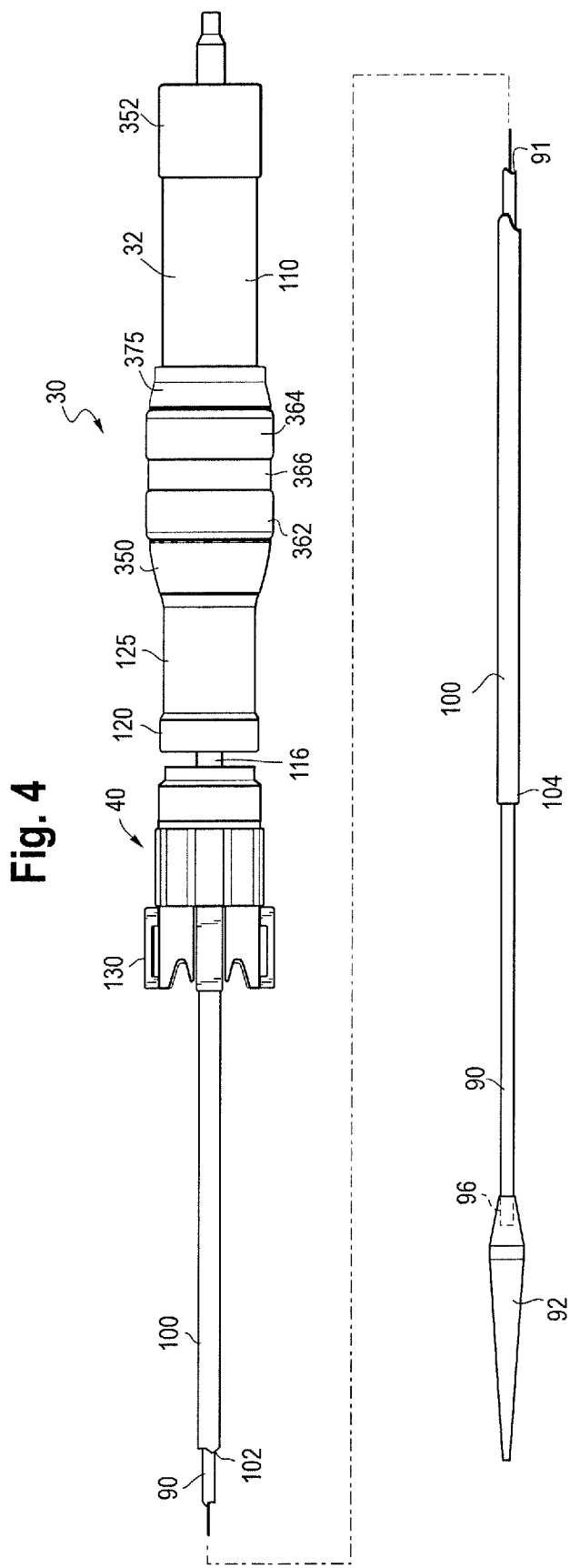

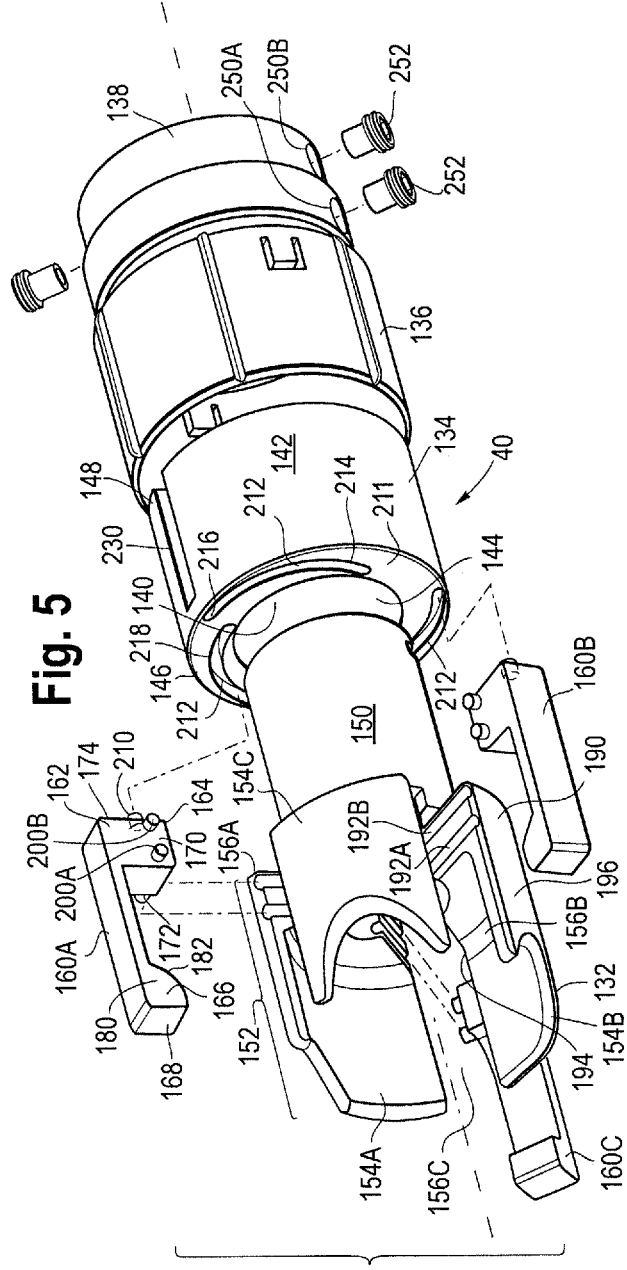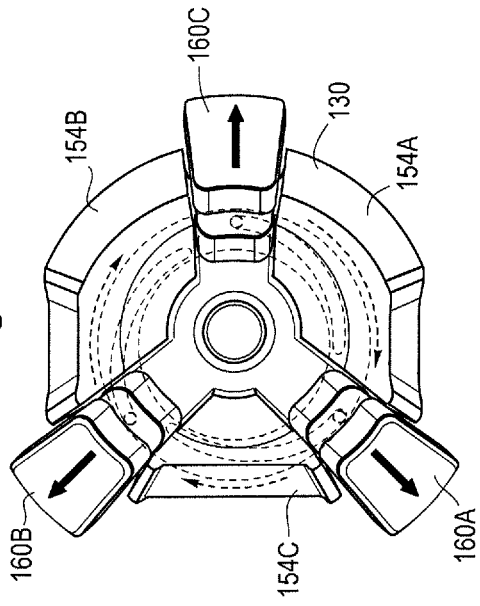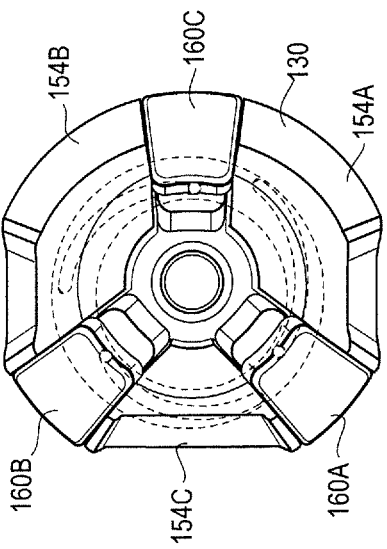

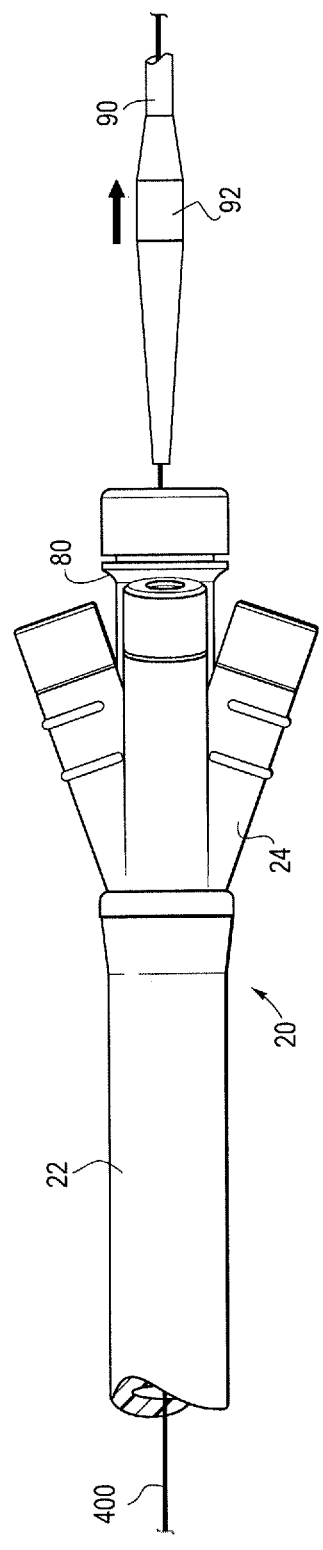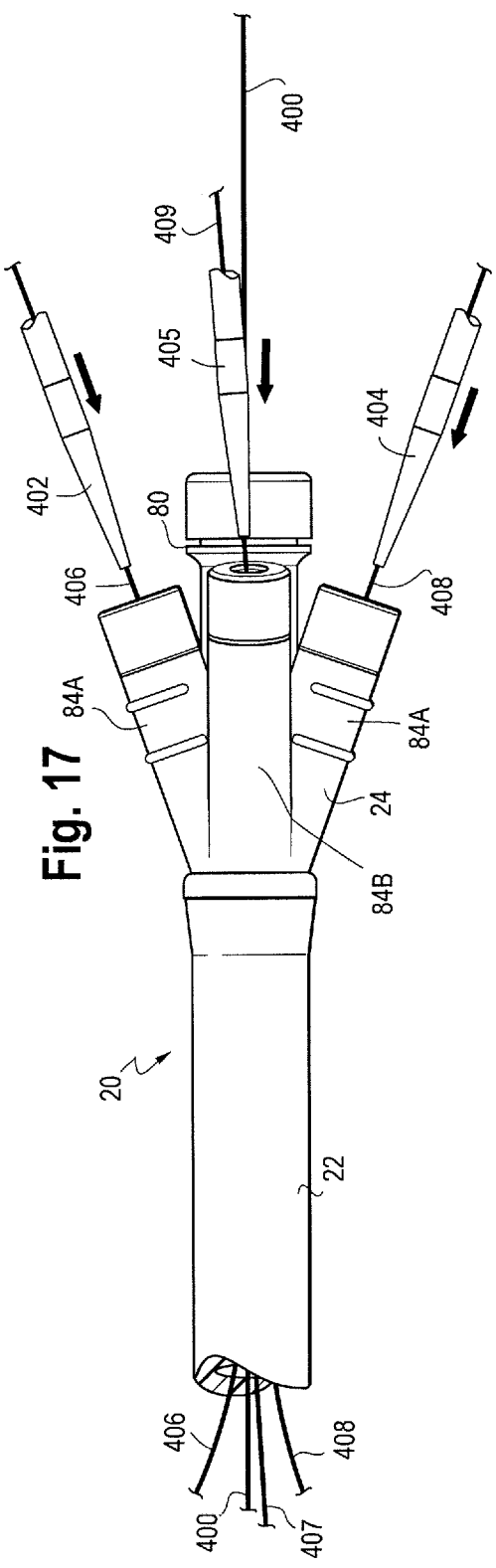

PROSTHESIS DELIVERY DEVICE WITH DETACHABLE CONNECTOR ASSEMBLY

CROSS-REFERENCE TO RELATED APPLICATIONS

This application claims priority and the benefit of U.S. provisional Patent Application Ser. No. 62/448,106, filed Jan. 19, 2017, which is incorporated herein by reference in its entirety.

BACKGROUND

This present disclosure relates generally to medical devices and methods of using the same, and more particularly, to an endovascular prosthesis delivery device and methods for placement and deployment of the prosthesis in the lumen of a vessel.

The use of delivery devices or introducers employing catheters are used for a variety of medical procedures, including procedures for establishing, re-establishing or maintaining passages, cavities or lumens in vessels, organs or ducts in human and veterinary patients, occlusion of such vessels, delivering medical treatments, and other interventions. For these procedures, an implantable medical device is delivered by means of a catheter, often intraluminally. For example, a stent, stent-graft, vena cava filter or occlusion device may be delivered intraluminally from the femoral artery, via a transapical approach and/or using other acceptable delivery locations and methods for deployment of the prosthesis.

For procedures in which a prosthesis or other medical device is implanted into a patient, the prosthesis is normally held on a carrier catheter or cannula of the introducer in a compressed state and then released from the cannula so as to expand to its normal operating state. In many devices, the steps to carry out the implantation may occur, for example, first by retracting an outer sheath away from the loaded prosthesis to allow for its expansion, and then performing further steps, for example, to release one or both ends of the prosthesis, deploy an anchoring stent, or the like. The prosthesis which is to be implanted within a patient's vasculature by the delivery device may vary depending on various factors including the procedure being performed and the portion of the vasculature being treated. Because there is an increasing complexity and variety of vascular anatomies targeted for treatment, there is a need for improved delivery devices and methods.

SUMMARY

In one example, a prosthesis delivery device is disclosed. The device includes an elongate sheath extending about a longitudinal axis. The sheath includes a sheath lumen longitudinally defined therein. A hub is coupled to the sheath, and includes a longitudinal hub lumen defined therein in communication with sheath lumen. A handle is distal to the hub. A connector assembly is coupled to a proximal end of the handle. The connector assembly is removably coupled to the hub, and the connector assembly includes a longitudinal passageway defined therein in communication with the longitudinal hub lumen. In another example, the handle includes a connector rod movably received within the handle bore, and the connector assembly is coupled to the connector rod. The connector assembly includes an attachment configuration and a detachment configuration. In the attachment configuration, the connector assembly is coupled to the hub, and the handle is operable to longitudinally move the connector rod, the connector assembly, the hub and the sheath together. In the detachment configuration, the connector assembly is detached from the hub.

In another example, a method of using a prosthesis delivery device is disclosed. The method includes one or more of the following steps. A step includes providing a delivery device including a sheath extending from a hub, a handle coupled to the hub via a connector assembly, an elongate member proximally extending from the handle through the connector assembly, through the hub, and into the sheath. A step includes longitudinally moving the sheath relative to the elongate member by actuation of the handle. A step includes detaching the connector assembly from the hub. A step includes removing the handle, the connector assembly, and the elongate member from the hub and the sheath.

Other devices, systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 illustrates an example of a prosthesis delivery device.

FIG. 2 is a side view of an example of a sheath assembly of the delivery device of FIG. 1.

FIG. 3 is a distal end view of the sheath assembly of FIG. 2.

FIG. 4 is a side view of an example of a catheter-handle assembly of the delivery device of FIG. 1.

FIG. 5 is a perspective exploded part view of an example of a connector assembly.

FIGS. 6A-6B are proximal end views of the connector assembly with jaw elements, depicting the jaw elements being displaced radially outward from an inner position.

FIG. 16 depicts a method of use of the prosthesis delivery device, with the removal of the catheter-handle assembly from the sheath assembly.

FIG. 17 depicts a method of use of the prosthesis delivery device, with auxiliary devices being used within the sheath assembly.

DETAILED DESCRIPTION OF THE PREFERRED EMBODIMENTS

Figure 7:
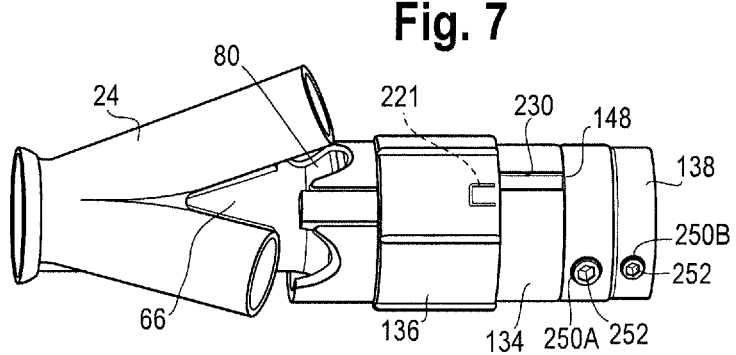
FIGS. 7-10 depict operation of the connector assembly.

The delivery device and methods described herein may deploy a wide range of different prostheses including, but not limited to cuffs, single lumen tubular stent grafts, bifurcated AAA stent grafts, branched or fenestrated stent grafts and combinations thereof. In addition to facilitating the delivery of a wide range of prostheses, the delivery device and methods may allow a variety of delivery approaches to be utilized, including but not limited to transapical or femoral approaches. More specifically, disclosed herein is a delivery device and methods for temporary coupling and manipulation of a sheath assembly, such as, for example, a tri-port sheath. A detachable connector assembly is provided for the increasing complexity ad variety of medical procedures, such as, for example, aneurismal anatomies targeted for treatment. The detachable connector assembly may provide advantages such as, for example, freeing space in the outer sheath by removal of the main prosthesis delivery core components. The additional space gained may allow larger sized ancillary devices to be deployed within the implanted outer sheath. In addition, a combination of prostheses can be deployed within the same outer sheath device. This arrangement may provide greater flexibility for the operator physician and should speed up procedure times for certain medical procedures. The connector assembly may be simple and intuitive and may allow simple longitudinal withdrawal after detachment. The connector assembly may be integrated with the handle, which may allow both to be removed in a single action. The guide wire cannula and the pusher catheter may be integrated with the handle and the connector assembly. The handle is operable to provide controlled retraction of the outer sheath for delivery.

In the present application, the term "proximal" when referring to a delivery device or stent graft refers to a direction that is farthest away from an operator using a delivery device and closest to the aorta, while the term "distal" refers to a direction that is generally closest to the operator using the delivery device. The distal and proximal ends of a delivery device may also be referred to as an introduction end of the delivery device and an operator end of the delivery device, respectively. The term "operator end" of the delivery device is that portion of the device that is intended to remain outside of a patient during a procedure. The term "introduction end" of the delivery device, which is opposite to the operator end, is that portion of the device that is intended to be inserted within a patient during a procedure.

FIG. 1 depicts an example of a pre-loaded prosthesis delivery device 10 disposed about a longitudinal axis LA, which may be deployed into the patient by the known Seldinger method. The delivery device 10 includes a sheath assembly 20 having an outer sheath 22 and a sheath hub 24. A handle-catheter assembly 30 is shown disposed relative to the sheath assembly 20. The handle-catheter assembly 30 includes a handle 32 that is distal to the sheath hub 24, and a connector assembly 40 that is disposed between the handle 32 and the sheath hub 24. The connector assembly 40 is operable for removably coupling to the sheath hub 24. A prosthesis 50 is retained within the outer sheath 22 in a prosthesis retention region 52.

FIG. 2 depicts an example of the sheath assembly 20. The outer sheath 22 includes an elongated sheath body 60 and a sheath lumen 62 longitudinally disposed therein about the longitudinal axis LA between a distal end 63 and a proximal end 65 of the outer sheath. The sheath hub 24 is securely coupled to the outer sheath 22. For example, the proximal end of the sheath hub 24 may be configured to receive the distal end 63 of the outer sheath 22, where is bonded with an adhesive, such as a heat or ultra-violet light activated adhesive.

The sheath hub 24 includes a longitudinal passageway 64 defined therein about the longitudinal axis LA. An axial hub connector port 66 may be disposed to distally extend away from the body of the sheath hub 24. The axial hub connector port 66 may be formed as a tubular housing with an axial hub lumen 70 defined therein disposed about the longitudinal axis LA. The axial hub lumen 70 is in fluid communication with the longitudinal passageway 64 and the sheath lumen 62. A hemostatic seal 72 may be housed within the axial hub lumen 70 of the axial hub connector port 66, as shown in FIG. 3. A flushing port 74 may extend from the body of the sheath hub 24 and is in fluid communication with the longitudinal passageway 64 and the sheath lumen 62. The flushing port 74 may be used for the flushing of a lubricious solution or the flushing out of air. A radial outward flange 80 may be disposed along a distal edge 82 of the axial hub connector port 66.

In FIG. 3, one or more side hub connector ports (three shown—84A, 84B, 84C) may be included, extending away from the sheath hub obliquely or orthogonal relative to the longitudinal axis LA. For example, each of the first, second, and third side hub connector ports 84A, 84B, 84C may be formed as a tubular housing with a side port lumen 86 defined therein, such as shown in side hub connector port 84A. A hemostatic seal 88 may be housed within the side port lumen 86 of each of side hub connector ports 84A, 84B, 84C. In one example, each side port lumen 86 is in fluid communication with the longitudinal passageway 64 and the sheath lumen 62. Alternatively, one or more of the side port lumens 86 may be in fluid communication with discrete longitudinal lumens defined the sheath wall, which may be at least partially separated from the sheath lumen 62 by a wall. The sheath hub 24 may be further configured as a CAPTOR™ valve, which may be provided by Cook Medical Inc., Bloomington, Ind.

FIG. 4 depicts an example of the handle-catheter assembly 30. At least one elongate member, such as a cannula and/or internal catheter may be extended from the handle. In one example, an elongated guide wire cannula 90 is shown extending out of the connector assembly 40. The elongated guide wire cannula 90 includes a guide wire lumen 91 longitudinally extending therein about the longitudinal axis LA. As will be described, the guide wire cannula 90 includes a distal end 94 securely coupled to the handle 32 and extends by a length beyond the proximal end 65 of the outer sheath 22, as shown in FIG. 1. A nose cone dilator 92, also shown in FIG. 1, may be securely coupled to a proximal end 96 of the guide wire cannula 90 to provide less traumatic tracking of the delivery device. The nose cone dilator 92 may include a proximal taper or rounded end and a distal axial recess to receive the proximal end 96, which may be bonded with an adhesive, such as a heat or ultra-violet light activated adhesive. An axial bore extends through the nose cone dilator 92, which is in communication with the guide wire lumen 91, to allow the guide wire to pass through the guide wire cannula 90 and out the nose cone dilator 92. A distally opening capsule (not shown) at a distal end of the nose cone dilator 92 may be included to form a top cap assembly, which is configured for the receipt of an exposed stent of the prosthesis 50.

FIG. 4 also depicts a pusher catheter 100 coaxially disposed over the guide wire cannula 90, extending out of the connector assembly 40. The pusher catheter 100 includes a pusher lumen 102 longitudinally extending therein about the longitudinal axis LA. As will be described, the pusher catheter 100 includes a distal end 103 securely coupled to the handle 32 and extends by a length short of the proximal end 65 of the outer sheath 22, as shown in FIG. 1. This arrangement defines a longitudinal aspect of the prosthesis retention region 52 between a proximal end 104 of the pusher catheter 100 and the proximal end 65 of the outer sheath 22. An annular space of the prosthesis retention region 52 is defined between the outer surface of the guide wire cannula 90 and the inner surface of the outer sheath 22. The prosthesis 50 is loaded and remains within the prosthesis retention region 52 during delivery. The outer sheath 22 is shown coaxially disposed over portions of the pusher catheter 100 and the guide wire cannula 90.

Returning to FIG. 4, the handle 32 may include a cylindrical housing 110 disposed about the longitudinal axis LA. A handle longitudinal passageway 112 is defined by the housing 110. A connector rod 116 is movably received within the handle longitudinal passageway 112. A proximal end 118 of the connector rod 116 extends beyond a proximal end 120 of the housing 110. The handle 32 may include an actuator operable to controllably move the connector rod. For example, a rotatable actuator 125 may be disposed along the proximal end 120 of the housing 110. The rotatable actuator 125 based on rotation relative to the housing 110 causes longitudinal displacement of the connector rod 116 between a top end extended position for prosthesis delivery (FIG. 1) and a bottom end retracted position for prosthesis deployment (FIG. 4).

The connector assembly 40 is coupled to the proximal end 118 of the connector rod 116 such that longitudinal displacement of the connector rod 116 causes longitudinal displacement of the connector assembly 40. The connector assembly 40 includes a connector end 130 operable for removably coupling to the sheath hub 24. To this end, the connector assembly 40 includes an attachment configuration and a detachment configuration.

In the attachment configuration shown in FIG. 1 and FIG. 7, the connector end 130 of the connector assembly 40 is coupled to the radial outward flange 80 of the axial hub connector port 66 of the sheath hub 24. In response to operation of the handle 32, and in particular, the rotation of the rotatable actuator 125, the connector rod 116 and the connector assembly 40 move as a unit to retract or extend the sheath assembly 20, relative to the fixed position of the pusher catheter 100 and the guide wire cannula 90. This configuration may permit distal retraction of the outer sheath 22 away from the nose cone dilator 92 to expose the prosthesis 50 for radial expansion and deployment. In the detachment configuration shown in FIG. 4 and FIG. 10, the connector end 130 is detached from the radial outward flange 80 of the axial hub connector port 66 of the sheath hub 24 such that the guide wire cannula 90 and/or the pusher catheter 100 can be removed from the sheath lumen 62 of the outer sheath 22.

FIG. 5 illustrates one example of the connector assembly 40, including a connector end housing 132, an actuating ring 134, a locking ring 136, and an end housing cap 138. The actuating ring 134 defines a tubular member having a longitudinal bore 140 extending therethrough about the longitudinal axis LA. The actuating ring 134 includes an outer surface 142 and a bore facing inner surface 144 separated from one another by a material thickness to define the wall of the actuating ring 134, extending between a proximal end 146 and a distal end 148 of the actuating ring 134.

The connector end housing 132 may include a distally extending barrel hub 150 that is received within the bore 140 of the actuating ring 134. A proximal housing portion 152 extends proximally from the barrel hub 150. One or more longitudinal slots are defined by the proximal housing portion 152. In an example, three longitudinal finger elements 154A, 154B, 154C may extend proximally from the barrel hub 150 such that one of the slots 156A, 156B, 156C is defined by adjacently located finger elements. The slots 156A, 156B, 156C may be formed equidistant from one another, for example, at 120 degrees apart. In another example, the proximal housing portion 152 including the finger elements 154A, 154B, 154C protrudes radially outward from the barrel hub 150 in order to have a greater diameter than the barrel hub 150.

Jaw elements 160A, 160B, 160C are disposed within corresponding slots 156A, 156B, 156C. The jaw element 160A will be now described as representative of the jaw elements 160B, 160C. The jaw element 160A has a longitudinal body that may be sized with a width and a length similar to the dimension of the corresponding slot 156A. The jaw element 160A includes a base 162 at its distal end 164 and a tip 166 at its proximal end 168. The base 162 and the tip 166 may protrude radially inward relative to the thin body of the jaw element disposed between the base 162 and the tip 166. In one example, the base 162 may include a pair of lateral planar surfaces 170, 172 disposed opposite from one another and a distally facing planar surface 174 interconnecting the lateral planar surfaces 170, 172. The tip 166 includes a protruding body 180 that may include a rounded surface 182. The tip and the base are spaced from one another to capture a portion of the radial flange of the sheath hub therebetween to inhibit relative movement of the flange within this spacing. In the attachment configuration, the tip 166 and/or the protruding body 180 of the jaw elements is engaged to the axial hub connector port 66 of the sheath hub 24 to capture the radial outward flange 80. The inner surface of a base 190 of each of the finger elements (shown in finger element 154C) have one or more channels defined therein. For example, a pair of channels 192A, 192B may extend from lateral edges 194, 196 of the finger elements in a parallel relationship.

Figure 9:
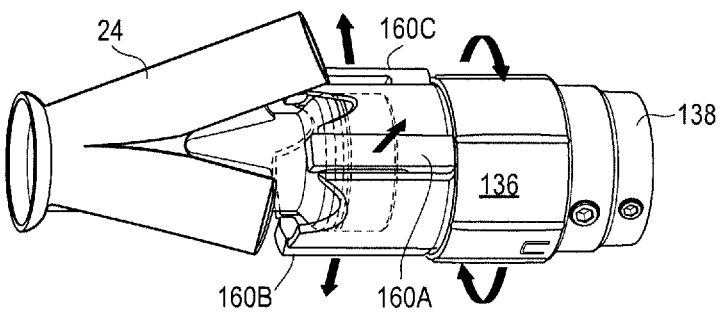
Figure 10:
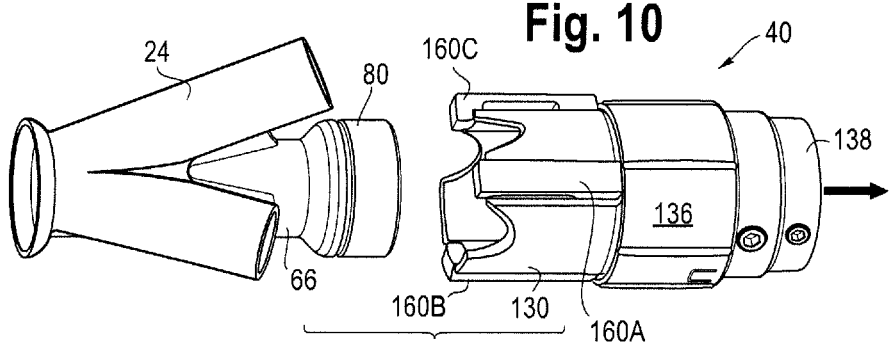

One or more protruding guides may extend away from each of the lateral planar surfaces 170, 172 of the jaw elements 160A, 160B, 160C for slidable movement within the channels 192A, 192B found in adjacent finger elements. For example, a pair of protruding guides 200A, 200B are shown extending away from each of the lateral planar surfaces 170, 172 of the jaw element 160A in a side-by-side relationship. The protruding guides 200A, 200B may have a circular cross-section (as shown) or other cross-sectional shapes that are sized to fit within the channels 192A, 192B. Each of the jaw elements 160A, 160B, 160C is coupled to corresponding adjacent finger elements with the protruding guides 200A, 200B inserted within the channels 192A, 192B for slidable movement in the radial direction. With reference to FIG. 6 and FIG. 9, each of the jaw elements 160A, 160B, 160C is operable to be radially displaced away from the longitudinal axis LA such that the tips clear the radial flange of the sheath hub for removal therefrom (as shown in FIG. 10). Lips may be formed along the ends of the channels 192A, 192B to prevent the protruding guides from sliding all the way out.

An axial protrusion 210 extends distally from the distally facing planar surface 174 of the jaw element. A proximally facing surface 211 of the proximal end 146 of the actuating ring 134 includes one or more axial guide recesses 212 (three guide recessed shown) formed therein. The guide recess 212 is shaped having an inclined shape such that a first end 214 of the guide recess 212 is radially disposed closer to the longitudinal axis LA than a second end 216 of the guide recess 212. Each of the jaw elements 160A, 160B, 160C is coupled to the actuating ring 134 with the respective axial protrusions 210 inserted within the corresponding guide recesses 212. In the attachment configuration, each of the jaw elements 160A, 160B, 160C is in a radially inward, engagement position, as shown in FIG. 6A, the respective axial protrusions 210 of the jaw elements 160A, 160B, 160C are at the first end 214 of the corresponding guide recesses 212, and the protruding guides 200A, 200B are at the first inner end of the channels 192A, 192B. In the detachment configuration, each of the jaw elements 160A, 160B, 160C is in a radially outward, disengagement position, as shown in FIG. 6B, the respective axial protrusions 210 are at the second end 216 of the corresponding guide recesses 212, and the protruding guides 200A, 200B are at the second end of the channels 192A, 192B. To activate radial displacement of each of the jaw elements 160A, 160B, 160C between the engagement position and the disengagement position, the actuating ring 134 is rotated relative to the fixed connector end 130, as shown in FIG. 9, the input force causes the walls 218 defining the respective guide recesses 212 to slidably engage the corresponding axial protrusions 210. Force is transferred to the protruding guides 200A, 200B to slidably engage the walls defining the channels 192A, 192B that is suitable to cause radial displacement of each of the jaw elements in either radial direction.

Figure 13:
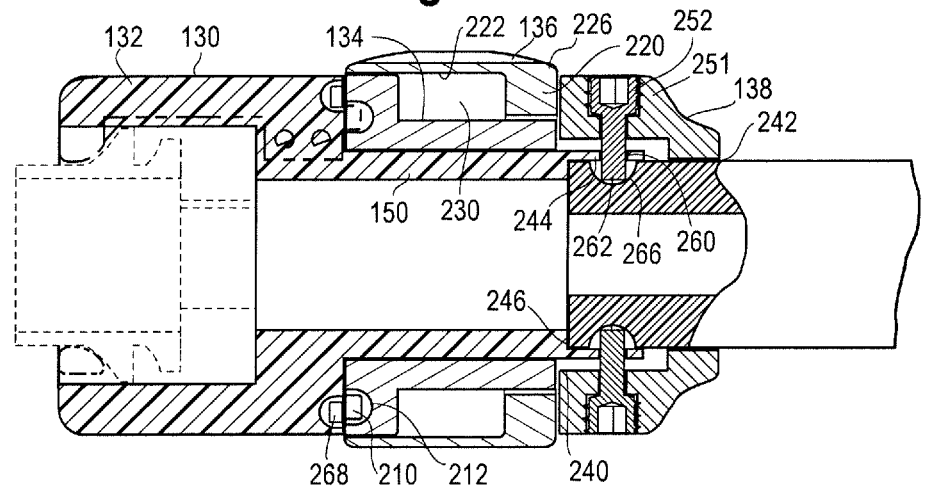
FIG. 13 is a detailed cross-sectional view of the connector assembly.

With additional reference to FIG. 13, the locking ring 136 is a tubular element that is sized to slidably fit over the actuating ring 134, the finger elements 154A, 154B, 154C of the connector end housing 132, and each of the jaw elements 160A, 160B, 160C when in the engagement position. The locking ring 136 includes one or more radially inward tabs 220 extending from an inner surface 222 of the locking ring 136. The tab 220 may be disposed at a distal end 226 of the locking ring 136. The tab 220 is placed into a ring channel 230 defined in the outer surface 142 of the actuating ring 134. The ring channel 230 extends from an intermediate zone of the actuating ring 134 to the distal end 148 of the actuating ring 134. In one example, a pair of tabs 220 may be placed 180 degrees apart from one another to fit within correspondingly placed ring channels 230.

Figure 8:
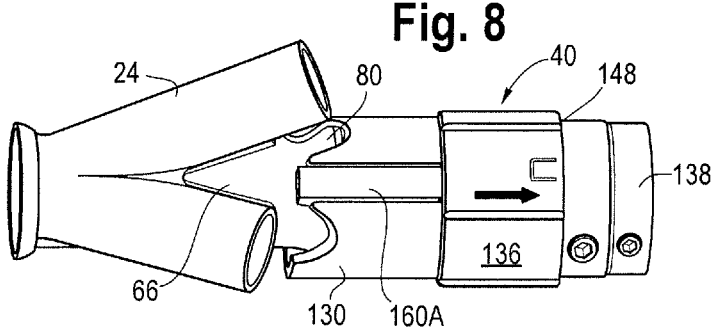

The locking ring 136 is slidable between a locking position, as shown in FIG. 7, and an unlocked position, as shown in FIG. 8. In the locking position, the tab 220 is placed closer to a first end 221 of the ring channel 230 than the distal end 148 of the actuating ring 134. Here at this position, at least a portion of the locking ring 136 may be placed over at least the distal end 164 of each of the jaw elements 160A, 160B, 160C. When the actuating ring 134 is attempted to be rotated, the locking ring 136 is positioned over the jaw elements 160A, 160B, 160C for maintaining engagement with the sheath hub and to inhibit radial displacement of the jaw elements. This arrangement also maintains the position of the respective axial protrusions 210 such that the actuating ring 134 is inhibited from rotation. The locking ring 136 is operable to prevent inadvertent rotation of the actuating ring 134 and disengagement of the connector end 130 from the sheath hub 24. In the unlocked position, the tab 220 is placed closer to the distal end 148 of the actuating ring 134 than the first end of the ring channel 230. Here at this position, no portion of the locking ring 136 is placed over the jaw elements 160A, 160B, 160C and the locking ring 136 is placed over the actuating ring 134. This arrangement permits the radial displacement of the jaw elements 160A, 160B, 160C.

With reference to FIG. 13, the end housing cap 138 is a ring shaped element having a proximal end opening 240 and a distal end opening 242. The distal end opening 242 may be sized to have a first inner cap diameter that is slightly larger than the diameter of the connector rod 116. The proximal end opening 240 may be sized to have a second inner cap diameter that is larger than the first inner cap diameter. The proximal end opening 240 is sized to receive the distal end of the barrel hub. A distal end 244 of the barrel hub 150 may have an internal flange 246 formed therein to form a barrel distal end internal diameter that is sized to receive the proximal end 118 of the connector rod 116. As shown, one or more sidewall threaded bores 250A and/or 250B may be formed through the entire sidewall 251 of the end housing cap 138. The sidewall threaded bores, which are shown 180 degrees apart, are configured to threadably couple to corresponding mechanical fasteners 252 such as setscrews or threaded pins. Sidewall threaded bores 250A are shown including a shoulder transition. When proximal sidewall threaded bores 250A are aligned with distal end sidewall bores 260 that are formed in the distal end 244 of the barrel hub 150, the mechanical fastener 252 may be inserted therein for securely coupling the end housing cap 138 to the barrel hub 150. Distal sidewall threaded bores 250B are disposed distal to the proximal sidewall threaded bores 250A. When mechanical fasteners 252 are inserted through the distal sidewall threaded bores 250B, tips 262 of the mechanical fastener 252 may be positioned within a radial groove 266 formed in the proximal end 118 of the connector rod 116. In this configuration, the connector rod 116 and the connector assembly 40 are coupled to one another for the transfer of axial force and movement therebetween, while rotation of the connector rod 116 may be allowed to occur without rotation or torque being transmitted to the connector assembly 40. To this end, rotation of the actuating ring 134 of the handle 32 for retraction of the outer sheath 22 may not affect the relative orientation of the sheath assembly 20 after insertion within the body. The connector rod 116 and the connector assembly 40 are configured to rotate independent from one another. Alternatively, the connector assembly 40 and the connector rod 116 may be securely coupled to one another such that axial forces and rotational torque are transmitted therebetween. For example, the tips 262 of the mechanical fastener 252 may be fixedly engage with the connector rod 116.

To assemble the connector assembly 40, the barrel hub 150 is inserted within the bore 140 of the actuating ring and the actuating ring 134 is slid down the barrel hub 150 until its distal end is exposed on the distal side of the actuating ring 134. The respective axial protrusions 210 are inserted within the corresponding guide recesses 212. A seal ring 268 may be disposed between the proximally facing surface 211 of the proximal end 146 of the actuating ring 134 and seal groove formed in the distally facing surface of the connector end housing. The tabs 220 of the locking ring 136 are then aligned with the corresponding ring channels 230 and the locking ring 136 is slid over the actuating ring 134. The end housing cap 138 is slid over the distal end of the exposed barrel hub and the respective sidewall bores are aligned to receive the mechanical fasteners for coupling the end housing cap to the barrel hub.

Other mechanisms and configurations of the jaw elements 160A, 160B, 160C may be utilized to provide radial displacement of the jaw elements. For example, the base 162 of the jaw elements may be pivotable attached to the connector end housing 132. A biasing member or spring may be associated with the jaw elements to maintain the jaw elements in the engagement position. A first end of an actuation wire or linkage may be coupled to the jaw elements. Tension applied to the actuation wire or linkage at a force sufficient to overcome the biasing force of the spring causes the jaw elements to pivot and be radially displaced outward to the disengagement position. Removal of tension permits the jaw elements to return automatically to the engagement position. Guide elements may be applied to the connector end housing to contain the actuation wire. A second end of the actuation wire or linkage may be coupled to the actuating ring 134 such that rotation of the actuating ring 134 provides suitable tension for pivoting. Alternatively, a sliding actuator sleeve may replace the actuating ring 134. The second end of the actuation wire or linkage may be coupled to the sliding actuator sleeve such that longitudinal displacement to the actuator sleeve provides suitable tension to pivot the jaw elements 160A, 160B, 160C toward the disengagement position. Alternatively, the jaw elements 160A, 160B, 160C may be radially displaced without an actuation wire or linkage. For example, a sliding actuator sleeve may replace the locking ring 136, and the jaw elements may be spring biased in the outward disengagement position. The jaw elements may be coupled to channels in the connector end housing, as described, or may be pivotably coupled. A biasing member or spring may be coupled between the connector end housing and the jaw elements. The sliding actuator is sized to fit and slide over the jaw elements and physically maintain them in the engagement position. The sliding actuator may slide away from the jaw elements to allow them to resiliently move to the biased disengagement position.

Figure 11:
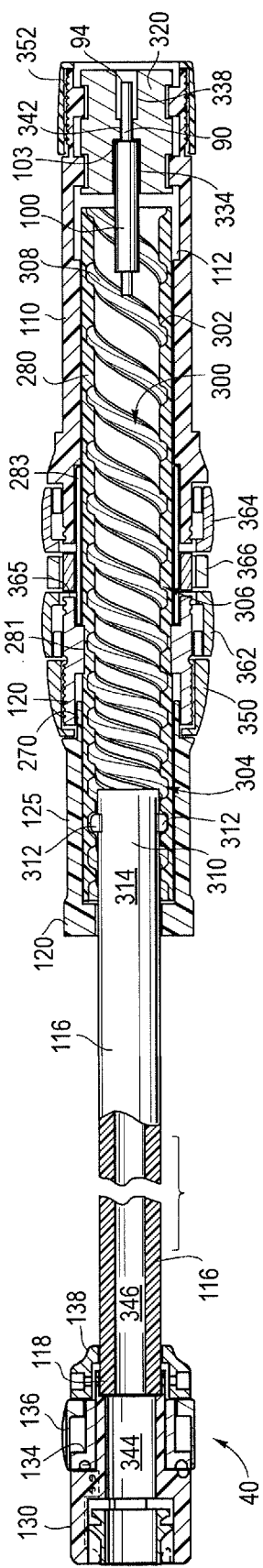
FIGS. 11-12 are longitudinal cross-sectional views of the catheter-handle assembly, depicting movement of the connector assembly relative to a handle.
Figure 12:
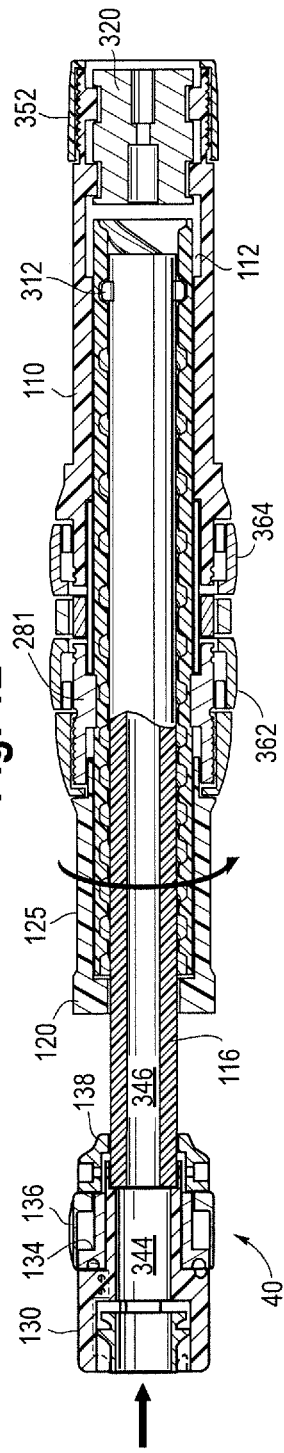
Figure 14:
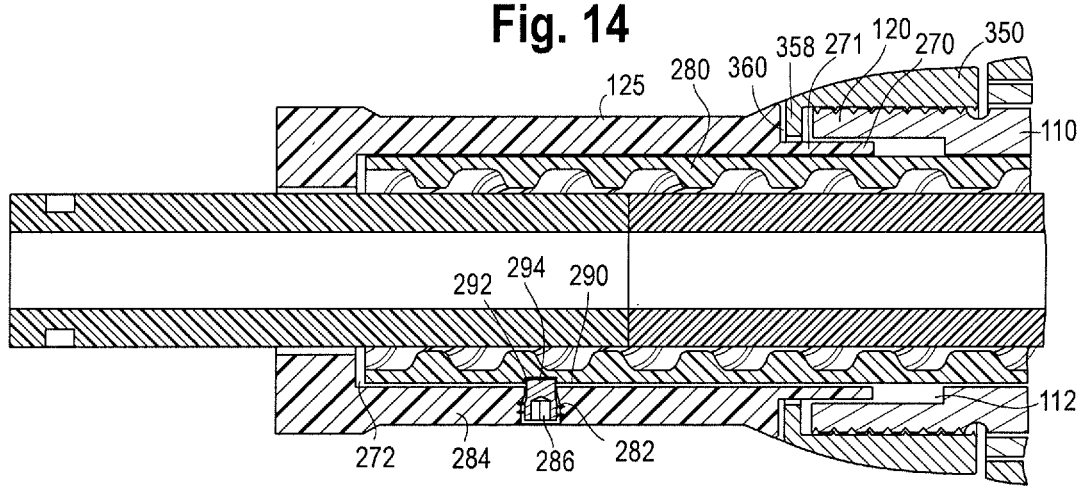
FIG. 14 is a detailed cross-sectional view of a rotatable actuator of the catheter-handle assembly.

FIGS. 11-12 depict operation and the internal make-up of the handle, including the cylindrical housing 110 and the handle longitudinal passageway 112. The distal end 270 of the rotatable actuator 125 is shown in FIG. 14 as a reduced diameter portion 271 of the rotatable actuator 125 that is inserted within the proximal end 120 of the housing 110. A longitudinal actuator bore 272 longitudinally extends in the rotatable actuator 125 and forms a proximal portion of the handle longitudinal passageway 112. A threaded tubular housing 280 is disposed within the handle longitudinal passageway 112. A mating boss 281 may extend radially toward the longitudinal axis LA from an inner surface 283 of the housing 110 for engagement with the threaded tubular housing 280, such as a radial groove formed in the threaded tubular housing, to inhibit longitudinal movement of the threaded tubular housing 280 relative to the housing 110. The threaded tubular housing 280 is shown extending beyond the proximal end 120 of the housing 110. The rotatable actuator 125 fits over the proximal end of the threaded tubular housing 280. With additional reference to FIG. 14, one or more fastener bores 282 are formed in the sidewall 284 of the rotatable actuator 125 and configured to receive a corresponding mechanical fastener 286, such as a setscrew. An outer surface 290 of the threaded tubular housing 280 may include a fastener recess 292 sized and shaped to receive a tip 294 of the mechanical fastener 286. Once the mechanical fastener 286 is threadably coupled within the fastener bore 282 and received in the fastener recess 292, the rotatable actuator 125 is securely coupled to the threaded tubular housing 280 such that in response to rotational input force being applied to the rotatable actuator 125, the force is transmitted to the threaded tubular housing 280. To this end, rotational movement of the rotatable actuator 125 in either direction causes rotation of the threaded tubular housing 280 in the same direction.

Returning to FIG. 11, the threaded tubular housing 280 includes a longitudinal housing bore 300 extending longitudinally extended therein about the longitudinal axis LA. The threaded tubular housing 280 includes a threaded internal surface 302 facing the housing bore 300. The threaded internal surface 302 may be a variable thread pitch. For example, a proximal portion 304 may include a first thread pitch, an intermediate portion 306 disposed distal to the proximal portion 304 may include a second thread pitch larger than the first thread pitch, and a distal portion 308 disposed distal to the intermediate portion 306 may include a third thread pitch larger than the second thread pitch.

The longitudinal housing bore 300 is sized to receive the connector rod 116 such that the rotatable actuator 125 and the housing 110, together with the threaded tubular housing 280 and the connector rod 116 are arranged in a coaxial relationship. A distal end 310 of the connector rod 116 may include a rod tab 312 or protruding body extending away from an outer surface 314 of the connector rod 116. The rod tab 312 is sized to fit within the threading formed into the threaded internal surface 302. To this end, rotation of the rotatable actuator 125 causes rotation of the threaded tubular housing 280 and the walls defining the threading defined by the threaded internal surface 302 slidably engages the rod tab 312. The slidable engagement and the pattern of such threading causes longitudinal displacement of the rod tab 312 within the threading and thus longitudinal displacement of the connector rod 116 relative to the rotatable actuator 125 and the housing 110. When the connector rod 116 is in its top end extended position, the rod tab 312 may operate as a physical stop when the rod tab 312 engages with the proximal internal end of the rotatable actuator 125. The rod tab 312 at its physical stop position would prevent inadvertent proximal movement of the outer sheath prior to delivery, and permit uni-directional rotation of the rotatable actuator. In an example, the first thread pitch of the proximal portion 304 may be sized for the greatest mechanical advantage for the operator because of the high retractions forces required to overcome the static forces and initiate movement of the outer sheath. In addition, the first thread pitch may be sized for finer and slower control of retraction of the outer sheath. In an example, the third thread pitch of the distal portion 308 may be sized for faster retraction of the outer sheath per a rotation of the actuator. In an example, the second thread pitch of the intermediate portion 306 may operate as a transition between the finer control retraction that may be required initially to the faster retraction that may be needed at the end of the retraction cycle.

Figure 15:
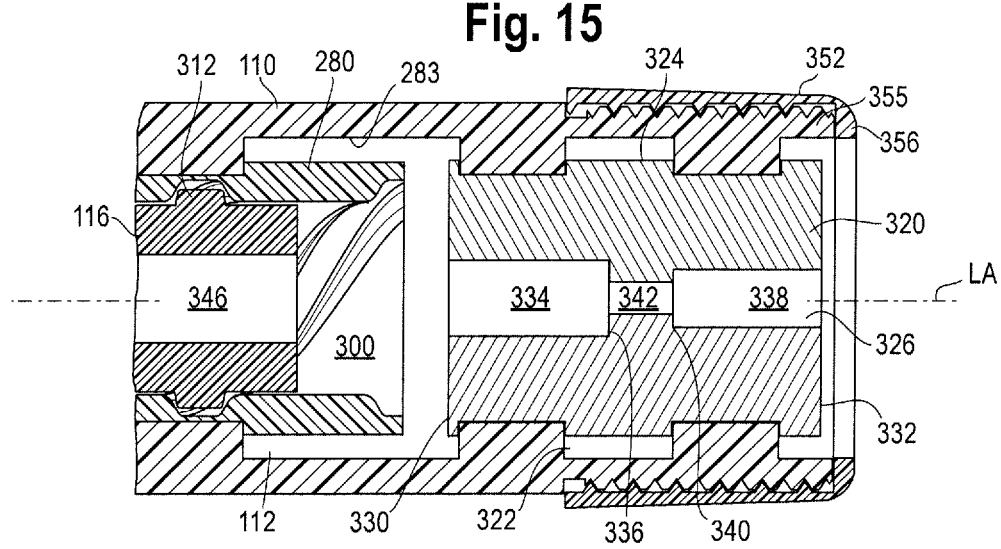
FIG. 15 is a detailed cross-sectional view of a distal end of the catheter-handle assembly.

With reference to FIG. 15, a cannula support element 320 may be disposed within a distal portion 322 of the longitudinal housing bore 300 of the housing 110. The cannula support element 320 is shaped as a cylindrical disk. The rounded outer surface 324 of the cannula support element 320 may be sized for engagement with the inner surface 283 of the housing 110. A longitudinal support bore 326 is formed through the cannula support element 320 about the longitudinal axis LA between a proximal face 330 and a distal face 332. The support bore 326 may include a proximal portion 334 extending from the proximal face 330 to a first intermediate location 336, a distal portion 338 extending from the distal face 332 to a second intermediate location 340, and an intermediate portion 342 extending between the first and second intermediate locations 336, 340. The cross-sectional area of the proximal portion 334 may be larger than the respective cross-sectional areas of the distal portion 338 and the intermediate portion 342. The cross-sectional area of the intermediate portion 342 may be smaller than the respective cross-sectional areas of the distal portion 338 and the proximal portion 334.

The guide wire cannula 90 extends distally through the connector end 130, a longitudinal hub bore 344 longitudinally extending through the barrel hub 150, and a longitudinal rod bore 346 longitudinally extending through the connector rod 116, and into the longitudinal housing bore 300 of the threaded tubular housing 280 and the handle longitudinal passageway 112. The distal end 94 of the guide wire cannula 90 is inserted through the proximal and intermediate portions 334, 342 and into the distal portion 338 of the longitudinal support bore 326, as shown in FIG. 11. The intermediate portion 342 is sized about the same size as the diameter of the guide wire cannula 90. A pin vice (not shown) may be inserted into the distal portion 338 from the distal side and be securely coupled to the distal end 94 of the guide wire cannula 90 such that the handle 32 is securely coupled to the guide wire cannula 90. The distal portion 338 is sized to receive diameter of the guide wire cannula 90 and the pin vice. The pin vice may be locked and may be released for selective longitudinal movement of the guide wire cannula 90 with respect to the handle 32. The distal end 94 of the guide wire cannula 90 may terminate in a luer connector to enable flushing liquid and radiopaque medium to be deployed through the delivery device.

The pusher catheter 100 is coaxially disposed over the guide wire cannula 90 and extends distally through the connector end 130, the longitudinal hub bore 344, and the longitudinal rod bore 346, and into the longitudinal housing bore 300 of the threaded tubular housing 280 and the handle longitudinal passageway 112. The distal end 103 of the pusher catheter 100 is inserted into the proximal portion 334 of the longitudinal support bore 326, as shown in FIG. 11. The proximal portion 334 is sized about the same size as the diameter of the pusher catheter 100. The distal end 103 may be securely coupled within the proximal portion 334 with an adhesive such that the handle 32 is securely coupled to the pusher catheter 100.

In FIG. 11, a proximal end cap 350 and a distal end cap 352 may be provided to be fitted around and about the proximal end 120 and a distal end 355 of the housing 110, respectively, to securely retain separate halves of the housing 110 of the handle 32 together, if desired. The distal end cap 352 may define a ring shaped element that is sized to fit over the distal end 355. In an example, the distal end 355, or ends of the halves together forming the distal end 355, may be externally threaded for coupling with internal threads provided along the inner surface of the distal end cap 352. With additional reference to FIG. 15, an axial lip 356 may extend radially inward from the distal end cap 352 to capture the cannula support element 320 within the handle. There may be a ring spacing defined between the axial lip and the support element 320 to receive a seal member. Returning to FIG. 14, the proximal end cap 350 may define a ring shaped element that is sized to fit over the proximal end 120. The proximal end cap 350, or ends of the halves together forming the proximal end 120, may be externally threaded for coupling with internal threads provided along the inner surface of the proximal end cap 350. A radial lip 358 is shown extending inward from the proximal end cap and disposed between the axial face of the proximal end 120 and the flange 360 formed by the transition of reduced diameter portion 271 to the body of the rotatable actuator 125.

FIG. 11 also shows one or more trigger wire release mechanisms or rotatable rings 362, 364 disposed over a portion of the housing 110. Distal ends of the trigger wires (not shown) may be coupled to the inner surface of the trigger wire release mechanisms or rotatable rings 362, 364.

In one example, the distal ends of the trigger wires may be coupled to the inner surface of the proximal trigger wire rotatable ring 362 by a setscrew, by adhesives, welding or any other suitable attachment mechanisms. From the attachment point on the inner surface of the proximal rotatable trigger wire ring 362, the trigger wires may extend through one or more openings or apertures 365 formed in the sidewall of the housing 110 of the handle 32. In one non-limiting example, the trigger wire may extend from the handle, within the pusher catheter 100, to an end of the prosthesis 50. The distal trigger wire rotatable ring 364 may be adjacent to or abut the proximal trigger wire rotatable ring or, as shown in FIG. 11, a spacer element 366, such as a stationary spacer ring, may be positioned between the proximal and distal trigger wire rotatable rings 362, 364. If present, the stationary spacer ring may be coupled to the outer surface of the housing 110 such as by adhesives, bonding, snap-fit, screws or other suitable attachment mechanisms. The presence of the spacer element 366 may reduce the risk of the user inadvertently rotating the proximal trigger wire rotatable ring 362 and the distal trigger wire rotatable ring 364 at the same time, if simultaneous rotation of the respective rotatable rings is not desired.

As shown in FIG. 1, the distal end 370 of the proximal end cap 350 may include a set of ratcheting teeth 372 which extend at least partially circumferentially around the distal end of the proximal end cap 350 and which point in a distal direction. The ratcheting teeth 372 are configured to engage in a correspondingly shaped set of proximally facing ratcheting teeth formed in a proximal ratchet ring that is positioned underneath and within the proximal trigger wire rotatable ring 362. The proximal ratchet ring may be integrally formed with the inner surface of the proximal trigger wire rotatable ring 362 or, alternatively, the proximal ratchet ring may be a separately formed component which is received within the inner surface of the proximal trigger wire rotatable ring or otherwise secured (such as by adhesives, welding or other attachment mechanisms) to the inner surface of the proximal rotatable ring. The proximal ratchet ring may rotate along with the proximal trigger wire rotatable ring 362 and ensures uni-directional rotation of the proximal rotatable ring in a first direction while preventing the proximal rotatable ring from rotating in a direction opposite to the first direction.

A series of ratcheting teeth 374 may be formed on a ringed protrusion 375 extending away from the outer surface of the housing 110 of the handle 32 and which extend at least partially circumferentially around the outer surface. The ratcheting teeth 374 may point in a proximal direction and are configured to engage in a correspondingly shaped set of distally facing ratcheting teeth formed in a distal ratchet ring that is positioned underneath and within of the distal trigger wire rotatable ring 364. The distal ratchet ring may be integrally formed with the inner surface of the distal trigger wire rotatable ring 364 or, alternatively, the distal ratchet ring may be a separately formed component which is received within the inner surface of the distal trigger wire rotatable ring 364 or otherwise secured (such as by adhesives, welding or other attachment mechanisms) to the inner surface of the distal rotatable ring. The distal ratchet ring may rotate along with the distal trigger wire rotatable ring 364 to ensure uni-directional rotation of the distal trigger wire rotatable ring in a first direction while preventing the distal trigger wire rotatable ring from rotating in a direction opposite to the first direction. Separate ratcheting mechanisms, such as the proximal ratcheting ring ensures uni-directional rotation of the proximal trigger wire rotatable ring 362 while the distal ratcheting ring ensures uni-directional rotation of the distal trigger wire rotatable ring 364.

When deployment is desired, distal retraction of the trigger wires (such as by manipulation of one or both of trigger wire rotatable rings 362, 364 allows the proximal ends of the trigger wires to be released from the proximal end of the prosthesis 50 and pulled distally through the pusher catheter 100, allowing the proximal end of the prosthesis 50 to at least partially deploy radially outwardly within a vessel. If other diameter reducing ties are being used to radially restrain the proximal end of the prosthesis 50, those ties must also be removed by manipulation of one or both of the trigger wire rotatable rings 362, 364 to allow the proximal end of the prosthesis to fully deploy from the guide wire cannula 90 within the vessel.

At least a portion of the outer surface of the handle 32, the rotatable actuator 125, and the actuating ring 134 may include a gripping portion for a physician to grip with one hand while manipulating the respective components. The gripping portion is preferably ergonomically shaped for user comfort, and may be covered in a layer of softer plastic or rubber or have a gripping surface to ensure a stable grip. The gripping portion may include a series of protrusions or ridges formed in the respective outer surface of the components.

The respective components of the handle 32, the connector rod 116, and the connector assembly 40 may be injection molded as a single unitary structure or alternatively, may comprise upper and lower parts or halves that clam shell, lock, snap-fit or are otherwise securable to each other such as, for example, by welding, bonding and/or adhesives. The respective components of the handle 32, the connector rod 116, and the connector assembly 40 may be constructed of a variety of materials, including but not limited to acrylonitrile butadiene styrene (ABS) or a similar thermoset plastic, polymers, metals (aluminum, stainless steel) and/or composites (carbon, fiberglass), for example.

The guide wire cannula 90 may be made of a variety of suitable materials that are stiff, yet flexible enough to allow the guide wire cannula to conform to the tortuous anatomy of a patient during use, and may be either straight or have a curve imparted to a portion of it. For example, the guide wire cannula may be constructed of polymers, metals and/or alloys, including nitinol or stainless steel. The pusher catheter 100 and/or the sheath 22 may be constructed from various materials, and in one example, a proximal portion of the pusher catheter which is introduced into the patient may comprise a polymer, sometimes referred to as VRDT (or vinyl radiopaque dilator tubing), plastics, metals, alloys or a combination thereof, whereas a distal portion of the pusher catheter may comprise the same material as the proximal portion of the pusher catheter or it may be a different material including but not limited to plastics, polymers, alloys, metals or a combination thereof, that provide sufficient maneuverability and stiffness to the pusher catheter as necessary and desired.

Each of the seals or seal rings 72, 88, 268 is configured to prevent back flow of fluid or unintended leakage through the ports. The seal(s) may be rings, discs or other suitable valving mechanisms made from silicones, rubbers, plastics or other materials.

The prosthesis 50 may include any type of implantable medical device, such as a cuffs, stent grafts (single lumen, bifurcated AAA, branched, or fenestrated and combinations thereof) stents, vena cava filters, or occlusion devices. In one example, the prosthesis is a stent graft including a tubular body of a biocompatible graft material such as Dacron, expanded PTFE or Thoralon, a polyurethane material. The stent graft is supported by self-expanding stents (not shown for clarity). The proximally extending exposed stent assists with providing infra-renal fixation of the deployed stent graft. The stent graft may include fenestrations formed in the graft body, which are provided to give access to the renal arteries. The stent graft may be retained on the delivery device by retention of the exposed stent into the capsule or diameter reducing ties of the delivery device and distally by the trigger wire retention. In the diameter reduced condition, movement of the stent graft is still possible, whereas when released to full diameter this may not be possible.

In FIG. 2, the flushing port 74 may be extended from the sheath hub 24. The flushing port 74 defines a fluid path in communication with the sheath lumen 62. Another fluid conduit (not shown) may be extended from the handle 32, which defines a fluid path in communication with the pusher lumen 102. These fluid conduits enable flushing fluid, radiopaque medium, or other gas or liquid to be deployed through the delivery device.

Alternatively, the handle 32 may not be operable for sheath retraction and/or include trigger wire actuators. In other words, the handle may include a cylindrical housing having a portion securely coupled to the end cap housing of the connector assembly 40 or otherwise coupled to the connector assembly. The guide wire cannula and the pusher catheter may extend from such housing and configured for relative movement therebetween. To this end, the housing may be unlocked and retracted distally relative to the guide wire cannula and the pusher catheter, which retracts the sheath as described herein. After the connector assembly is placed in the disengagement configuration, as described herein, and the housing is locked (with pin vice or screw) to the guide wire cannula and the pusher catheter, the handle-catheter assembly may be removed from the sheath assembly, as described herein.

A method of using one of the examples of the delivery device 10 within the body vessel of a patient will now be described. While the delivery device may be generally discussed in relation to a stent graft and method of deployment thereof into one or more specific arteries, including the aorta and iliac arteries, it may be also contemplated that the delivery device and methods may relate to any prosthesis and/or any body or vessel lumen in which such a deployment is necessary or desired.

The delivery device 10 is placed in its delivery configuration as shown in FIG. 1. Here, the connector assembly is in the attachment configuration, such that the connector assembly, the connector rod, the sheath hub and the outer sheath move together. For example, the jaw elements of the connector assembly may be radially displaced inward for coupling to the radial flange about the hub edge of the sheath hub. The connector rod is at its top end extended position, shown in FIG. 1 and FIG. 11. One or more elongate members, such as the guide wire cannula and/or the pusher catheter, are disposed within the longitudinal rod bore of the connector rod, the longitudinal hub bore of the connector assembly, the handle bore of the hub, and within the sheath lumen of the sheath, as shown in FIG. 1. The proximal end of the pusher catheter is located distal to the proximal end of the outer sheath to define the prosthesis retention region, where the prosthesis is loaded on the wire guide cannula and radially compressed, such as shown in FIG. 1. The locking ring may be slid over the connector end in its locking position.

The proximal end or introduction end of the delivery device 10 in its delivery configuration may be introduced into the body vessel over a previously inserted guide wire correctly taking into account N-S position as well as rotational position with respect to target vessels. When the prosthesis 50 is a fenestrated stent graft, markers on stent graft body and around the fenestrations may be visualized for the correct orientation relative to the branch vessels. The delivery device 10 is tracked and advanced over the guide wire to the target treatment site with the body vessel.

With the connector assembly in its attachment configuration about the sheath hub, the rotatable actuator is rotated in a first direction, relative to the handle housing, causing the rotation of the threaded tubular housing. This rotation causes the walls defining the threading of the threaded internal surface to slidably engage the rod tab. In turn, the rod tab follows the threading to cause longitudinal displacement of the rod tab within the threading and thus longitudinal displacement of the connector rod, the connector assembly, the sheath hub, and the outer sheath relative to the guide wire cannula and the pusher catheter to expose the prosthesis for radial expansion and deployment. Withdraw the outer sheath while continuing to check position until the proximal end of the prosthesis is exposed. At this stage, the distal end of the prosthesis may be still retained by distal fixation or retention device, as described above, and the proximal end of the prosthesis may be retained by the retention devices, as described above, and the full expansion of the prosthesis may be restricted by the diameter reducing ties.

Distal retraction of the trigger wires by manipulation of one or both of proximal and distal trigger wire rotatable rings may allow the proximal ends of the trigger wires to be released from the proximal and distal ends of the prosthesis and pulled distally through the pusher catheter, allowing the proximal end of the prosthesis to at least partially deploy radially outwardly within a vessel.

Once the stent graft is fully deployed, the connector assembly is moved to the detachment configuration. Here, the locking ring may be slid over the actuating ring to its unlocked position. The actuating ring is rotated in a first direction to activate the connector end, or the outward radial displacement of each of the jaw elements to the disengagement position. The input force in rotating the actuating ring causes the walls defining the guide recesses to slidably engage the corresponding distally extending axial protrusions. In turn, force is transferred to the protruding guides to slidably engage the walls defining the channels that are suitable to cause outward radial displacement of the jaw elements. In the detachment configuration, the handle-catheter assembly 30 can be removed to a position outside of the outer sheath 22 and sheath hub 24, as shown in FIG. 16. To this end, the guide wire cannula 90 and the pusher catheter are disposable outside the sheath lumen, and ideally removed from the outer sheath to allow for full access to the sheath lumen, while the outer sheath remains within the body vessel at the target site about the guide wire.

FIG. 17 depicts access sheaths 402, 404, 405 may be advanced on their respective indwelling guide wires 406, 408, 409 through the side hub connector ports 84A, 84B, 84C of the sheath hub 24 and may be directed to the lumen of the prosthesis to or through the fenestration. With the removal of the guide wire cannula and the pusher catheter, larger sized sheaths and catheter devices may be inserted within the sheath lumen than what would be typical when the guide wire cannula and the pusher catheter inserted. The first access sheath is positioned at the opening of the fenestration. The dilators of the access sheaths are removed. An additional catheter and additional guide wire (4-5 Fr) may be advanced through the access sheaths and into the target vessel (e.g. renal artery). The additional catheter may have a crooked or hockey stick tip to facilitate access. The guide wire is removed from the additional catheter and a stiffer wire is re-inserted into the target vessel. One at a time, the access sheaths are withdrawn from the target vessels and covered stents are deployed between the fenestrations and target vessels. A balloon expanded device may be used to balloon expand if necessary for flaring portion of the covered stent within the fenestration of the main stent graft. Access sheaths are then removed and the guide wires are also removed from the target vessels and withdrawn from the system. The sheath assembly may then be withdrawn or the outer sheath may be left in place for further deployments. Further deployment may include a bifurcated distal component.

In one example, a method of using a prosthesis delivery system, including one or more of the following steps. Providing a delivery system including a sheath extending from a hub, a handle coupled to the hub via a connector assembly, an elongate member proximally extending from the handle through the connector assembly, through the hub, and into the sheath. Longitudinally moving the sheath relative to the elongate member by actuation of the handle. Detaching the connector assembly from the hub. Removing the handle, the connector assembly, and the elongate member from the hub and the sheath. Detaching a plurality of radially displaceable jaw elements of the connector assembly from the hub by rotating an actuating ring disposed on the connector assembly.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A prosthesis delivery device comprising:
   an elongate sheath extending about a longitudinal axis, the sheath including a sheath lumen longitudinally defined therein;
   a hub coupled to the sheath, the hub including a longitudinal hub lumen defined therein in communication with sheath lumen;
   a handle distal to the hub;
   a connector assembly coupled to a proximal end of the handle, wherein the connector assembly is removably coupled to the hub, and the connector assembly includes a longitudinal passageway defined therein in communication with the longitudinal hub lumen,
   wherein the connector assembly comprises a plurality of radially displaceable jaws, and the connector assembly includes an attachment configuration and a detachment configuration, wherein, in the attachment configuration, each of the jaws has an engagement tip coupled to the hub.

2. The device of claim 1, wherein the hub includes a radial flange about a hub edge defining the longitudinal hub lumen, and, in the attachment configuration, the engagement tip is coupled to the radial flange.

3. The device of claim 1, wherein the connector assembly includes an actuating ring operable to move the radially displaceable jaws between the attachment and detachment configurations.

4. The device of claim 3, wherein the connector assembly includes a locking mechanism operable to selectively maintain the radially displaceable jaws in an engagement position.

5. The device of claim 4, wherein the hub includes one or more side ports extending obliquely relative to the longitudinal axis, and the hub includes a hemostatic seal disposed within the longitudinal hub lumen.

6. The device of claim 1, further comprising a guide wire cannula proximally extending from the handle, and a pusher catheter proximally extending from the handle, wherein the pusher catheter is coaxially disposed over the guide wire cannula.

7. A prosthesis delivery device comprising:
an elongate sheath extending about a longitudinal axis, the sheath including a sheath lumen longitudinally defined therein;
a hub coupled to the sheath, the hub including a longitudinal hub lumen defined therein in communication with sheath lumen;
a handle distal to the hub;
a connector assembly coupled to a proximal end of the handle, wherein the connector assembly is removably coupled to the hub, and the connector assembly includes a longitudinal passageway defined therein in communication with the longitudinal hub lumen, wherein the handle comprises a handle bore longitudinally extending therein, and a longitudinally displaceable connector rod extending from the handle bore, wherein the connector assembly is coupled to a proximal end of the connector rod and,
wherein the connector assembly includes an attachment configuration and a detachment configuration, wherein, in the attachment configuration, the connector assembly is coupled to the hub, and the connector assembly, the sheath, and the hub are longitudinally movable during longitudinal displacement of the connector rod, and
wherein the handle comprises a rotatable tubular actuator and a handle tubular housing disposed longitudinally from the rotatable tubular actuator, together defining the handle bore, the handle comprising a threaded tubular housing disposed within the handle bore, the threaded tubular housing is securely coupled to the rotatable actuator, and a distal end of the connector rod coupled within the threaded tubular housing, wherein, in response to rotation of the rotatable tubular actuator, rotation of the threaded tubular housing causes longitudinal displacement of the connector rod.

8. A prosthesis delivery device comprising:
an elongate sheath extending about a longitudinal axis, the sheath including a sheath lumen longitudinally defined therein;
a hub coupled to the sheath, the hub including a longitudinal hub lumen defined therein in communication with sheath lumen;
a handle distal to the hub, the handle having a handle bore longitudinally defined therein, the handle including a connector rod movably received within the handle bore;
a connector assembly coupled to the connector rod, the connector assembly having an attachment configuration and a detachment configuration, wherein, in the attachment configuration, the connector assembly is coupled to the hub, and the handle is operable to longitudinally move the connector rod, the connector assembly, the hub and the sheath together, and, in the detachment configuration, the connector assembly is detached from the hub,
at least one elongate member proximally extending from the handle, wherein, in the attachment configuration, the at least one elongate member is disposed within a longitudinal rod bore defined in the connector rod, a longitudinal hub bore defined in the connector assembly, the handle bore of the hub, and within the sheath lumen of the sheath,
wherein the at least one elongate member comprises a guide wire cannula and a pusher catheter coaxially disposed over the guide wire cannula.

9. The device of claim 8, wherein, in the attachment configuration, a proximal end of the pusher catheter is distal to a proximal end of the sheath to define a prosthesis retention region to receive a prosthesis, and the handle is operable to longitudinally move the connector rod, the connector assembly, the hub and the sheath together relative to the proximal end of the pusher catheter to permit deployment of the prosthesis.

10. The device of claim 9, wherein, in the detachment configuration, the guide wire cannula and the pusher catheter are disposable outside the sheath lumen.

11. The device of claim 8, wherein the connector assembly comprises a plurality of jaw elements, and an actuating ring operable to move the jaw elements between the attachment configuration where the jaw elements are coupled to the hub, and the detachment configuration where the jaw elements are radially displaced and decoupled from the hub.

12. The device of claim 11, wherein each of the jaw elements comprises a distally extended protrusion, and the actuating ring comprises a proximally facing surface including an axial guide recess formed therein, wherein the guide recess receives the distally extended protrusion, and walls defining the guide recess slidably engage the distally extended protrusion to radially displace the jaw elements in response to rotation of the actuating ring.

13. The device of claim 8, wherein the connector rod and the connector assembly are configured to rotate independent from one another.

14. A method of using a prosthesis delivery device, comprising:
providing a delivery device including a sheath extending from a hub, a handle coupled to the hub via a connector assembly, an elongate member proximally extending from the handle through the connector assembly, through the hub, and into the sheath;
longitudinally moving the sheath relative to the elongate member by actuation of the handle;
detaching the connector assembly from the hub; and
removing the handle, the connector assembly, and the elongate member from the hub and the sheath;
wherein the detaching step further comprises detaching a plurality of radially displaceable jaw elements of the connector assembly from the hub by rotating an actuating ring disposed on the connector assembly.

* * * * *